(12) United States Patent
Sommers et al.

(10) Patent No.: US 12,285,199 B2
(45) Date of Patent: Apr. 29, 2025

(54) SURGICAL BONE RIVET

(71) Applicant: Acumed LLC, Hillsboro, OR (US)

(72) Inventors: Mark B. Sommers, Beaverton, OR (US); Andrew W. Seykora, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 408 days.

(21) Appl. No.: 17/712,487

(22) Filed: Apr. 4, 2022

(65) Prior Publication Data
US 2022/0313330 A1    Oct. 6, 2022

Related U.S. Application Data

(60) Provisional application No. 63/171,311, filed on Apr. 6, 2021.

(51) Int. Cl.
*A61B 17/86* (2006.01)

(52) U.S. Cl.
CPC ........ *A61B 17/8625* (2013.01); *A61B 17/864* (2013.01); *A61B 17/866* (2013.01)

(58) Field of Classification Search
CPC .. A61B 17/8625; A61B 17/864; A61B 17/844
See application file for complete search history.

(56) References Cited

U.S. PATENT DOCUMENTS

| 5,167,665 | A | 12/1992 | McKinney |
| 6,168,597 | B1 | 1/2001 | Biedermann et al. |
| 6,540,751 | B2 | 4/2003 | Enayati |
| 7,503,106 | B2 | 3/2009 | Crutchley et al. |
| 8,974,508 | B2 * | 3/2015 | Stephan ................. A61B 17/84 606/313 |

(Continued)

FOREIGN PATENT DOCUMENTS

| DE | 19543651 A1 | 7/1997 |
| EP | 2043537 B1 | 2/2011 |
| WO | 2011005788 A1 | 1/2011 |

OTHER PUBLICATIONS

International Search Report corresponding to related International Patent Application No. PCT/US2022/023320 mailed Jul. 12, 2022, 3 pages.

(Continued)

*Primary Examiner* — Olivia C Chang
(74) *Attorney, Agent, or Firm* — Knobbe, Martens, Olson & Bear, LLP (57) ABSTRACT

A bone rivet is provided that may be used as an alternative to a bone screw for bone fixation. The bone rivet includes a head and a threaded shaft that can be expanded upon installing the bone rivet into bone. A channel extends through the bone rivet and is shaped corresponding to a bulb of a mandrel used for installing the bone rivet. A first section of the channel has a smaller width than the mandrel's bulb to enable the bulb to expand the threaded shaft and a second section is sized to have a greater width. The installation process eliminates the task of rotating a typical bone screw during its installation. The threaded shaft also includes a cutting flute, which cuts a thread path for the threaded shaft into the bone thereby reducing the amount of torque needed to rotate and remove the bone rivet from bone.

12 Claims, 8 Drawing Sheets

(56) References Cited

U.S. PATENT DOCUMENTS

2012/0010668 A1    1/2012  Shimko

OTHER PUBLICATIONS

International Written Opinion corresponding to related International Patent Application No. PCT/US2022/023320 mailed Jul. 12, 2022, 7 pages.
International Preliminary Report corresponding to related International Patent Application No. PCT/US2022/023320 mailed Oct. 19, 2023, 9 pages.
European Extended Search Report corresponding to related European Patent Application No. 22785232.4 dated Nov. 5, 2024, 7 pages.

\* cited by examiner

SURGICAL BONE RIVET

PRIORITY CLAIM

The present application claims priority to and the benefit of U.S. Provisional Application 63/171,311, filed Apr. 6, 2021, the entirety of which is herein incorporated by reference.

BACKGROUND

Bone screws are typically the gold standard fracture fixation device for providing reliable and solid fixation of a fractured bone during the healing time period. In various examples, bone screws may be used as a stand-alone device to affix a bone fragment to a larger bone segment or as a lag screw, with multiple variations such as compression screws, cannulated screws, etc. Bone screws are also often used in conjunction with plating or intramedullary device technologies. Typical bone screws may be headed or headless and may employ numerous thread technologies and driver interface technologies.

Bone screw installation often requires rotating the screw to advance it into bone. Such an installation process can be time-consuming and can be especially arduous for a surgeon in some instances, such as when installing long screws with small pitches. One alternative bone fixation device to bone screws is a bone rivet. Installing typical bone rivets, however, may still require rotation of a component, and in some instances, may result in a portion of a deployment tool being left in a patient. It can also be difficult to remove typical bone rivets once installed, among other drawbacks.

Accordingly, a need exists for an alternative bone fixation device to bone screws that addresses the above drawbacks of typical bone screws and typical bone rivets.

SUMMARY

The present disclosure relates generally to bone fixation devices. More specifically, the present disclosure provides new and innovative bone rivets for bone fixation that may be used as an alternative to bone screws. The present disclosure also provides insertion systems and methods for installing the provided bone rivets.

In an example, a bone rivet includes a body portion having a head and a threaded shaft. At least a portion of the threaded shaft is deformable such that a width of the deformed at least a portion of the threaded shaft is greater than a width of the threaded shaft prior to deformation. A channel extends through the body portion, the channel including a first portion having a greater width than a second portion. The first portion of the channel extends through the head of the body portion. The body portion is constructed of a material such that the at least a portion of the threaded shaft deforms upon forced expansion of the at least a portion of the threaded shaft and subsequently maintains that deformation. The threaded shaft includes a cutting flute.

In another example, a bone rivet installation system includes a mandrel and the above example bone rivet. The mandrel includes a rod and a bulb. The bulb is at a distal end of the mandrel and has a greater width than the rod. The width of the bulb is greater than the width of the second portion of the bone rivet's channel and less than the width of the first portion of the bone rivet's channel.

In another example still, a bone rivet installation method includes drilling, via a drill, a hole into at least a first cortex of a bone. The above example bone rivet loaded with the above example mandrel is inserted into the drilled hole. The mandrel is then translated through the bone rivet's channel and out of the bone rivet thereby deforming the at least a portion of the bone rivet's threaded shaft such that the bone rivet is installed in the bone.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

DETAILED DESCRIPTION

The present disclosure provides a bone rivet that may be used as an alternative to a bone screw for bone fixation. For example, a surgeon may use the provided bone rivet as a stand-alone device to affix a bone fragment to a larger bone segment instead of using a bone screw. In some instances, a surgeon may use the provided bone rivet with plating or intramedullary device technologies.

The provided bone rivet includes a body having a head and a threaded shaft. The threaded shaft can be expanded upon installation of the bone rivet into bone so that the bone rivet provides holding power in the bone. In some examples, the threaded shaft can be constructed of a material such that the threaded shaft as a whole deforms to provide this expansion. In other examples, the threaded shaft can include one or more slits that separate the threaded shaft into two or more wings. In such other examples, the threaded shaft can be constructed of a material that enables the two or more wings to bend away from one another and maintain that bent position. The at least one thread on the threaded shaft provides increased holding power when the at least one thread is compressed into bone, as compared to a rivet with a shaft that is not threaded, and allows for controlled rotational removal of the rivet if so desired.

The provided bone rivet also includes an interior channel shaped corresponding to a bulb of a mandrel used for installation of the bone rivet. The bone rivet may be loaded with the mandrel during insertion of both into a bone hole, and then the mandrel may be translated through the bone rivet's interior channel and out of the bone rivet to install the bone rivet. A section of the interior channel is sized to have a smaller width (e.g., diameter) than the mandrel's bulb such that the bulb forces the portion of the bone rivet including this interior channel section to expand as the bulb is translated through this interior channel section. This interior channel section is within the threaded shaft. A different section of the interior channel is sized to have a greater width (e.g., diameter) than the mandrel's bulb such that the bulb can be translated through this different interior channel section without affecting the bone rivet. This different interior channel section is within the bone rivet's head, and at least in some instances, a portion of the threaded shaft.

Accordingly, the provided bone rivet can be installed by inserting the bone rivet loaded with a mandrel into a pre-drilled bone hole and removing the mandrel from the bone rivet. This installation process eliminates the time-consuming, and sometimes arduous, task of rotating a typical bone screw during its installation to drive the bone screw into bone. The provided bone rivet can therefore help reduce operative time and help reduce physical strain for a surgeon. In some aspects, the provided bone rivet and/or mandrel may be adapted to be used with a powered drill such that the bone rivet and/or mandrel are used to drill the bone hole, thereby eliminating the pre-drilling step and further reducing operative time.

Once the bone rivet is installed, it is also a requirement in orthopedic applications that a bone fixation device can be removed from the bone. The at least one thread of the threaded shaft helps enable removal of an installed bone rivet. The bone rivet's head may also include a driver interface that a surgeon may engage with a drive instrument during removal. For example, the surgeon may rotate the installed bone rivet with the drive instrument to remove the bone rivet in a similar fashion as removing a screw. Because the provided bone rivet is inserted and installed without rotating the bone rivet, however, a thread path does not exist in the bone, which can result in an undesired amount of torque being needed to remove the bone rivet. To help reduce the amount of torque needed to remove the bone rivet, the threaded shaft of the provided bone rivet may include a reverse cutting flute. The cutting flute cuts the thread path for the threaded shaft into the bone as the bone rivet is rotated thereby reducing the amount of torque needed to rotate and remove the bone rivet. The provided bone rivet is therefore easier to remove from bone once installed than at least some typical bone rivets.

Figure 1:
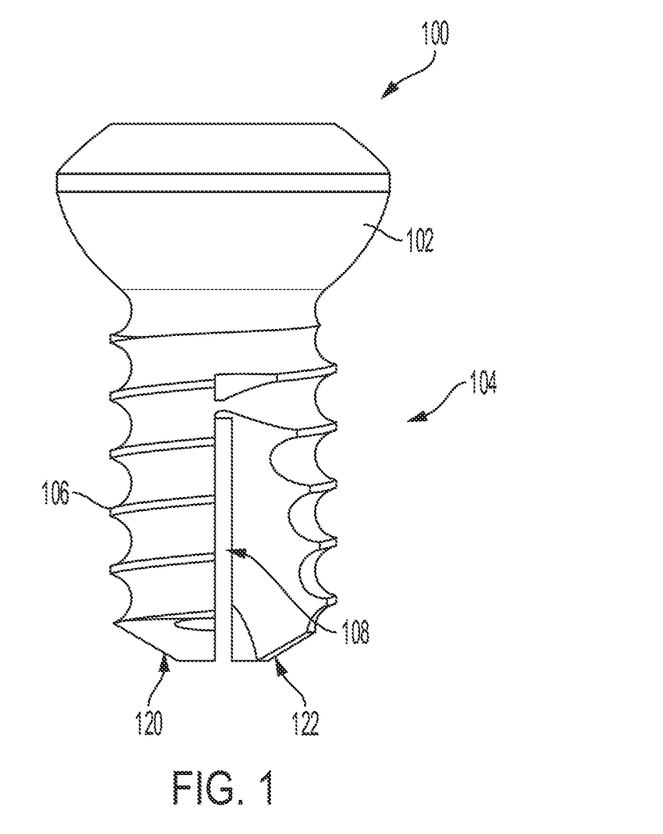
FIG. 1 illustrates a side view of a bone rivet, according to an aspect of the present disclosure.
Figure 2:
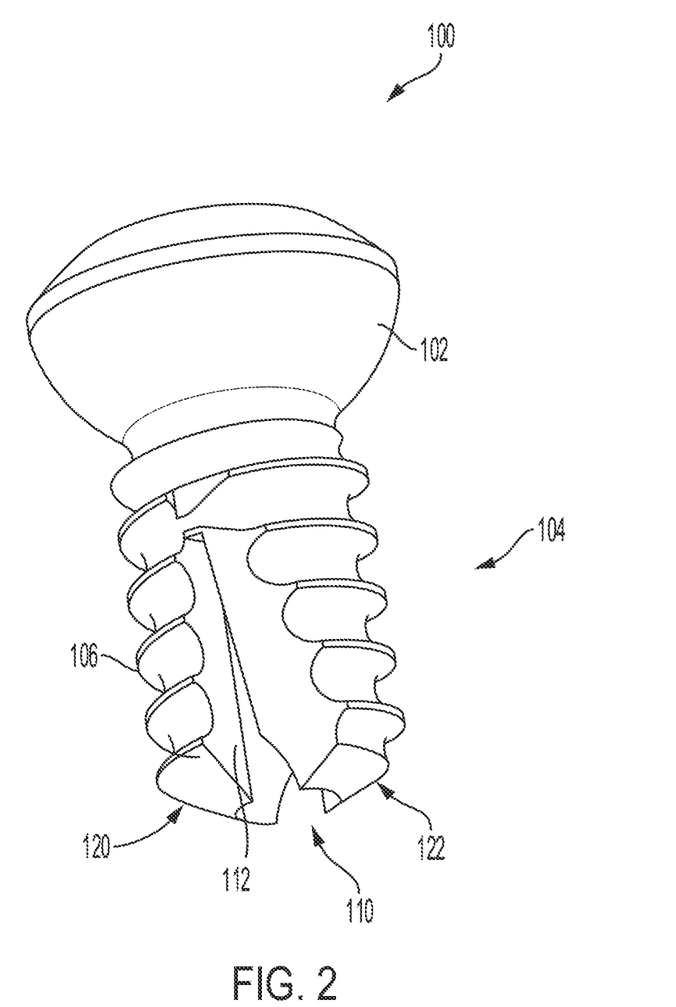
FIG. 2 illustrates a perspective view of the bone rivet of FIG. 1 relative to a leading end of the bone rivet, according to an aspect of the present disclosure.
Figure 3:
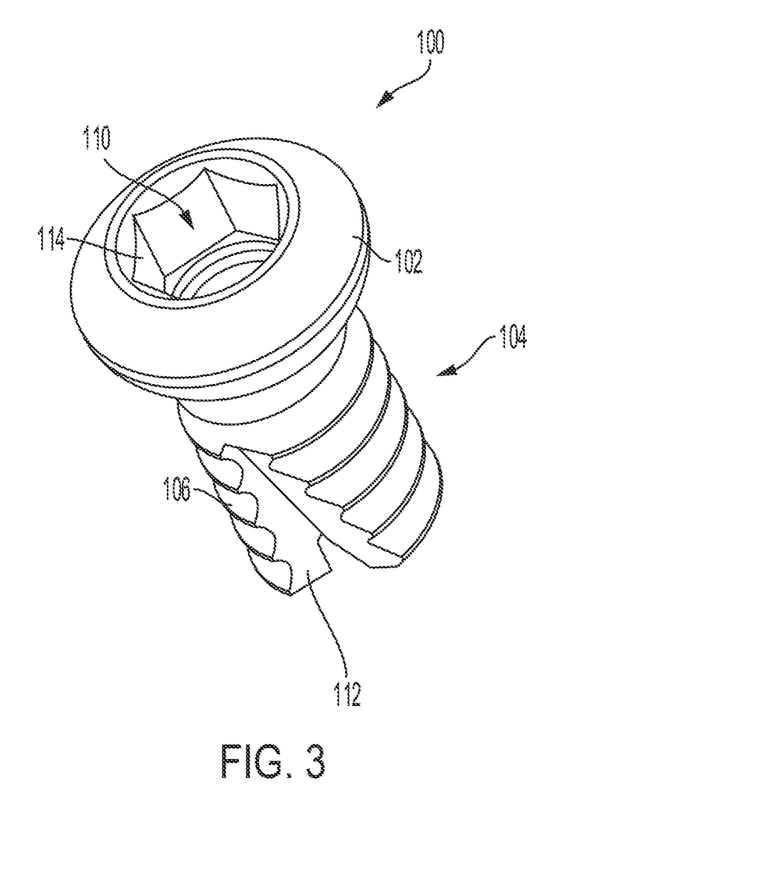
FIG. 3 illustrates a perspective view of the bone rivet of FIG. 1 relative to a trailing end of the bone rivet, according to an aspect of the present disclosure.

FIGS. 1 to 3 illustrate various views of an example bone rivet 100. The bone rivet 100 includes a body having a head 102 and a threaded shaft 104. A channel 110 extends through the body of the bone rivet 100 from a trailing end of the bone rivet 100 to a leading end of the bone rivet 100. The trailing end includes the head 102 and the leading end includes the threaded shaft 104. In at least some aspects, the head 102 of the bone rivet 100 includes a driver interface 114 that may engage with a drive instrument. The driver interface 114 is illustrated as a hexagon interface in the example of FIG. 3, though in other examples the driver interface 114 may have any other suitable shape for engaging with a drive instrument (e.g., hexalobe, slotted, phillips, etc.)

The threaded shaft 104 of the bone rivet 100 includes a thread 106. In some examples, the threaded shaft 104 may include more than one thread 106 such that the threaded shaft is double-threaded, triple-threaded, etc. The thread 106 of the threaded shaft 104 may be of any suitable thread form, such as trapezoidal, curved, sawtooth, etc. In one aspect of the present disclosure (e.g., FIGS. 8A and 8B), the threaded shaft 104 may continuously extend around the channel 110. In such an aspect, the thread 106 may extend continuously on the threaded shaft 104. In other aspects of the present disclosure (e.g., FIGS. 1-4), the threaded shaft 104 may include a slit 108 such that at least a portion of the threaded shaft 104 is split into a wing 120 and a wing 122. In such other aspects, the thread 106 is discontinuous on the threaded shaft 104 due to the slit 108. In some examples, the threaded shaft 104 may include more than one slit 108 such that at least a portion of the threaded shaft 104 is split into three or more wings 120, 122. For instance, the threaded shaft 104 may include two slits 108 perpendicular to one another thereby splitting the threaded shaft 104 into four wings 120, 122. In another instance, the threaded shaft 104 may include three slits 108 at an angle of 120° from one another and joining at a central axis of the bone rivet 100, thereby splitting the threaded shaft 104 into three wings 120, 122.

In at least some aspects, the threaded shaft 104 includes a cutting flute 112. The cutting flute 112 cuts into bone to form a thread path for the thread 106 when an installed bone rivet 100 is rotated, such as to remove the installed bone rivet 100 from bone. By forming the thread path for the thread 106, the cutting flute 112 helps reduce the amount of torque needed to rotate and remove an installed bone rivet 100 from bone. For instance, without a thread path in the bone, an undesirable amount of torque would be required to rotate an installed bone rivet 100, which could cause the driver interface 114 to strip or a drive instrument to break. In some examples, the cutting flute 112 may be located at an edge of the wing 120 or the wing 122 and adjacent the slit 108. The example illustrated in the figures shows the cutting flute 112 located at an edge of the wing 120 and adjacent the slit 108. In other examples, the cutting flute 112 may be located on the wing 120 or the wing 122, and away from the slit 108.

The threaded shaft 104 may be constructed of a material that enables at least a portion of the threaded shaft 104 to deform upon a sufficient force being applied to the threaded shaft 104, and to thereafter maintain that deformation. For example, the wing 120 and the wing 122 may be forced away from another such that they bend away from one another (FIG. 6C) and permanently maintain that bend against forces that may be experienced within the bone. Suitable materials for enabling the wing 120 and the wing 122 to bend and permanently maintain that bend include, for example, stainless steel, titanium, cobalt chrome, and some plastics such as PEEK, etc. In some aspects, the head 102 may also be constructed of this material such that the bone rivet 100 as a whole is constructed of a single material. In one aspect, the head 102 may be constructed of a different material than the threaded shaft 104.

In aspects in which the threaded shaft 104 includes one or more slits 108, the one or more slits 108 may determine the portion of the threaded shaft 104 that is deformed. Stated differently, the portion of the threaded shaft 104 including the one or more slits 108, which is the wings 120 and 122, may be the only portion of the threaded shaft 104 that deforms. In various aspects, a portion of the threaded shaft 104 that does not include the one or more slits 108, and therefore is not split into wings 120 and 122, does not deform upon installation of the bone rivet 100.

Figure 8A:
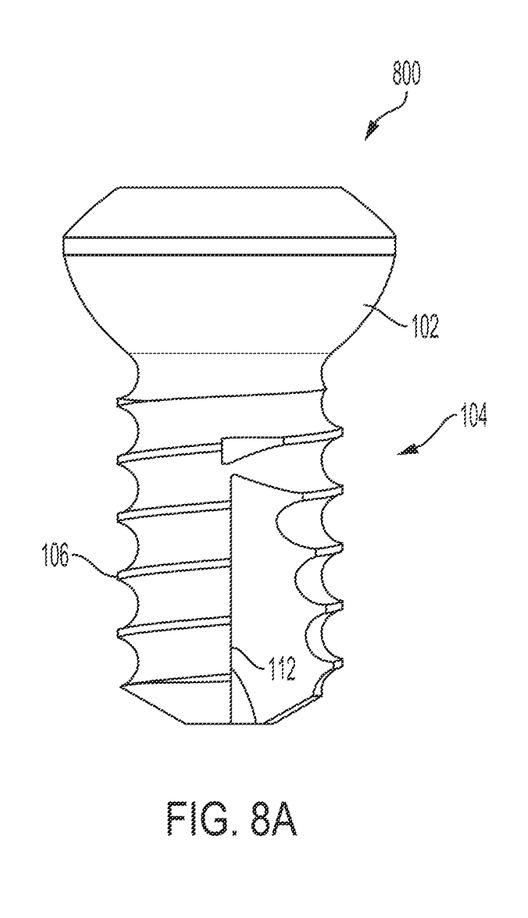
FIG. 8A illustrates a side view of a bone rivet with a continuous threaded shaft, according to an aspect of the present disclosure.
Figure 8B:
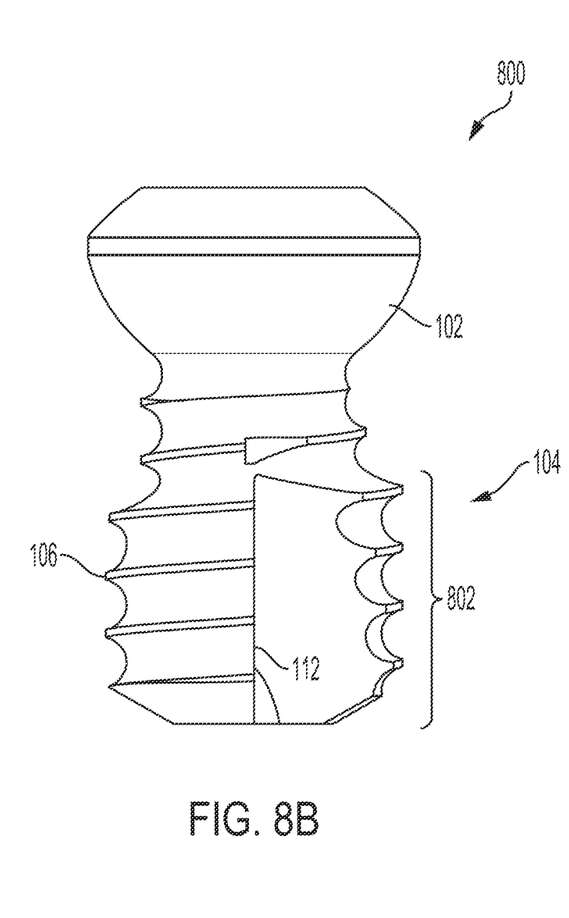
FIG. 8B illustrates a side view of the bone rivet of FIG. 8A having a threaded shaft with a deformed portion, according to an aspect of the present disclosure.

As mentioned above, in one aspect of the present disclosure, the threaded shaft 104 may continuously extend around the channel 110. Stated differently, in such an aspect, the threaded shaft 104 does not include the slit 108. FIG. 8A illustrates an example bone rivet 800 that includes a threaded shaft 104 that extends continuously around the channel. In this example, the cutting flute 112 is formed in the threaded shaft 104 without the slit 108. In such an aspect, when the example bone rivet 800 is installed, the threaded shaft 104 deforms so that a diameter of at least a portion of the threaded shaft 104 increases and the increased diameter is permanently maintained against forces that may be experienced within the bone. FIG. 8B illustrates the example bone rivet 800 with a deformed portion 802 of the threaded shaft 104 that has a greater diameter than a remaining portion of the threaded shaft 104. Suitable materials for enabling the threaded shaft 104 to deform and maintain that deformation in this way include, for example, stainless steel, titanium, cobalt chrome, and some plastics such as PEEK, etc. In at least some aspects, the head 102 may also be constructed of this material such that the bone rivet 100 as a whole is constructed of a single material. In one aspect, the head 102 may be constructed of a different material than the threaded shaft 104.

Figure 4:
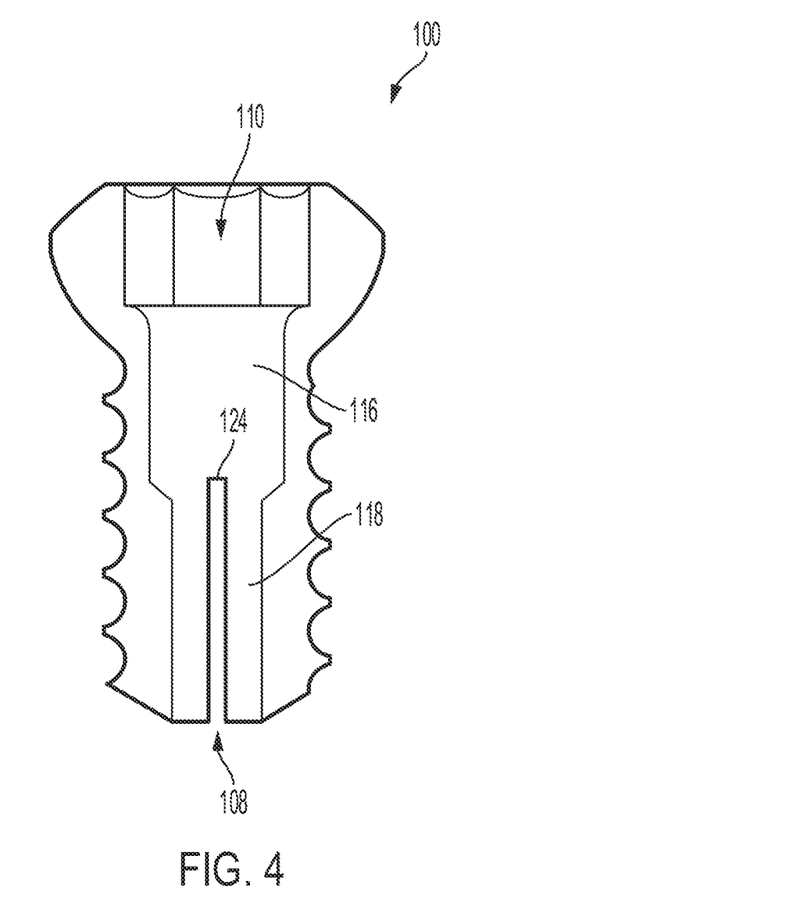
FIG. 4 illustrates a cross-sectional view of the bone rivet of FIG. 1 along a central plane of the bone rivet, according to an aspect of the present disclosure.

FIG. 4 illustrates a cross-sectional view of the bone rivet 100, along a central plane of the bone rivet 100, showing the channel 110 that extends through the body of the bone rivet 100. The channel 110 includes a first portion 116 and a second portion 118. The first portion 116 has a greater width than the second portion 118. In some aspects, the channel 110 may be cylindrical. In such aspects, the widths of the first portion 116 and of the second portion 118 are diameters. In other aspects, the channel 110 may be non-cylindrical (e.g., square, hexagonal, etc.). In some examples, such as the illustrated one, the width of the channel 110 may gradually increase from the second portion 118 to the first portion 116. In other examples, the width of the channel 110 may abruptly increase from the second portion 118 to the first portion 116.

Figure 5:
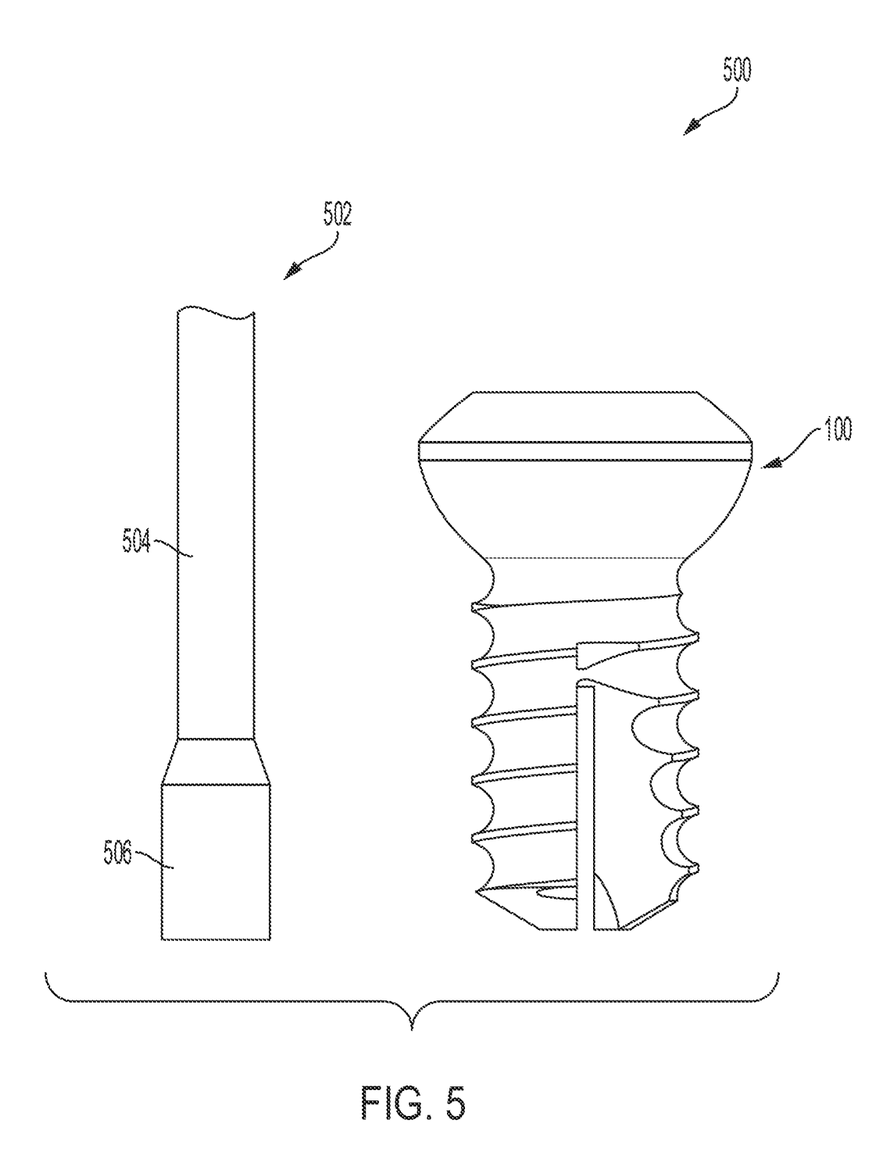
FIG. 5 illustrates a system including a mandrel and a bone rivet, according to an aspect of the present disclosure.

FIG. 5 illustrates an example bone rivet insertion system 500 that includes the bone rivet 100 and a mandrel 502. The example mandrel 502 includes a rod 504 and a bulb 506. The bulb 506 is located at a distal end of the mandrel 502. A proximal end (not illustrated) of the mandrel 502, in at least some aspects, may be adapted to be used with a bone rivet deployment tool (not illustrated). The bulb 506 has a greater width than the rod 504. In some aspects, the rod 504 and/or the bulb 506 of the mandrel 502 may be cylindrical. In such aspects, the widths of the rod 504 and/or the bulb 506 are diameters. In other aspects, the rod 504 and/or the bulb 506 of the mandrel 502 may be non-cylindrical (e.g., square, hexagonal, etc.). In some examples, such as the illustrated one, the width of the mandrel 502 may gradually increase from the rod 504 to the bulb 506. In other examples, the width of the mandrel 502 may abruptly increase from the rod 504 to the bulb 506.

The bone rivet 100 and the mandrel 502 are each adapted to be used in conjunction for installing the bone rivet 100 in bone. For instance, the bone rivet 100 may be loaded with the mandrel 502 such that the rod 504 is positioned through the channel 110 and a leading end of the bone rivet 100 is adjacent the bulb 506. The bone rivet 100 is shown loaded with the mandrel 502 in FIG. 6B discussed below. From the loaded configuration, the bulb 506 of the mandrel 502 may be translated through the channel 110 to install the bone rivet 100. Returning to FIGS. 4 and 5, the width of the bulb 506 is sized according to the widths of the first portion 116 and the second portion 118 of the channel 110 of the bone rivet 100. More specifically, the width of the bulb 506 is greater than the width of the second portion 118, but less than the width of the first portion 116. As such, when the bulb 506 is translated through the channel 110 from the loaded configuration, the bulb 506 forces the threaded shaft 104 to deform as the bulb 506 translates through the second portion 118 since the bulb 506 has a greater width than the second portion 118. For example, the wing 120 and the wing 122 may bend away from one another as the bulb 506 translates through the second portion 118.

A difference between the width of the bulb 506 and the width of the second portion 118 can determine an amount that the threaded shaft 104 deforms. For instance, the larger the width of the bulb 506 as compared to the width of the second portion 118, the more that the threaded shaft 104 will deform as the bulb 506 is translated through the second portion 118. In at least some aspects, the width of the bulb 506 is therefore more than marginally greater than the width of the second portion 118 so that the threaded shaft 104 deforms sufficiently for the bone rivet 100 to provide sufficient holding power in bone. An upper limit of the width of the bulb 506 corresponds to a width of the first portion 116, which is limited by the widths of the threaded shaft 104 and the head 102.

As the bulb 506 is translated through the channel 110 and reaches the first portion 116, the bulb 506 no longer forces the threaded shaft 104 to deform since the width of the bulb 506 is less than the width of the first portion 116. In at least some aspects, the width of the bulb 506 is marginally less than the width of the first portion 116 such that the bulb 506 maintains axial alignment with the first portion 116 as the bulb 506 is translated through the first portion 116.

In various aspects, the first portion 116 and the second portion 118 of the channel 110 may be arranged relative to the slit 108. In the example illustrated in FIG. 4, the first portion 116 of the channel 110 begins near (e.g., just prior to) a termination point 124 of the slit 108 relative to the leading end of the bone rivet 100. This example arrangement of the first portion 116 and second portion 118 of the channel 110 may help maintain the integrity and strength of the bone rivet 100 upon installation. For instance, the second portion 118 ending, and therefore the first portion 116 beginning, near (e.g., just prior to) the termination point 124 of the slit 108 helps prevent undesired deformation or breakage of the threaded shaft 104 outside of the wings 120 and 122, which could reduce the holding strength or fatigue life of the bone rivet 100.

In another example, the first portion 116 of the channel 110 may begin at a middle portion of the slit 108, away from the termination point 124. In this example, only a portion of the wings 120 and 122 would deform since only a portion of the wings 120 and 122 include the narrower second portion 118 of the channel 110. It is also contemplated that, in one example, the first portion 116 of the channel 110 may begin after the termination point 124 of the slit 108 relative to the leading end of the bone rivet 100. In such an example, the material of the bone rivet 100 may deform or fracture at the termination point 124 of the slit 108 to accommodate the bulb 506 translating through the second portion 118. Despite the deformation or fracture at the termination point 124, the bone rivet 100 in this example maintains sufficient strength for bone fixation.

Figure 6A:
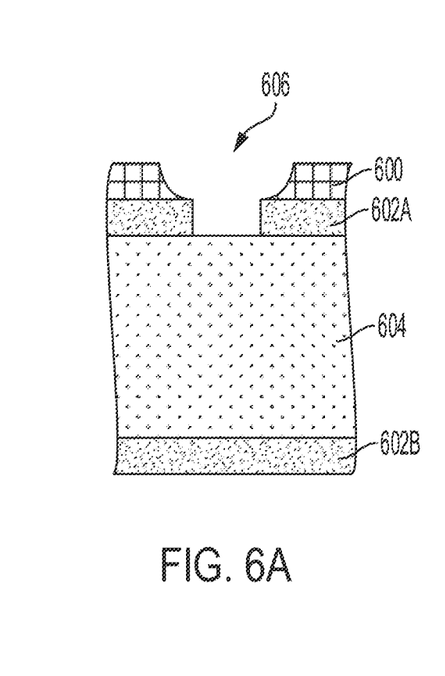
FIGS. 6A to 6C illustrate portions of a bone rivet insertion method, according to an aspect of the present disclosure.
Figure 6B:
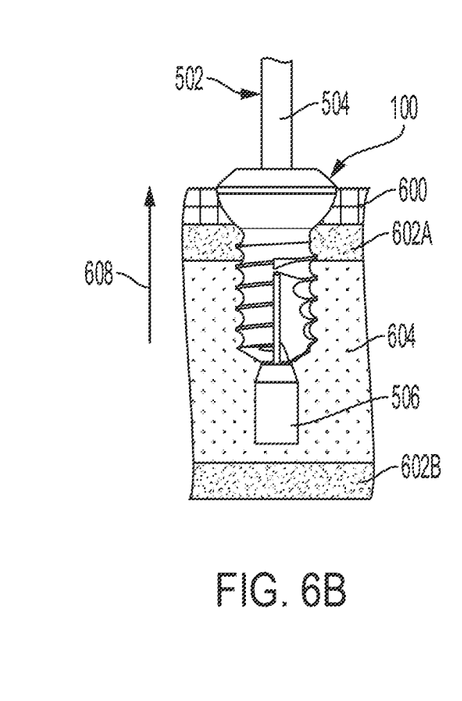
Figure 6C:
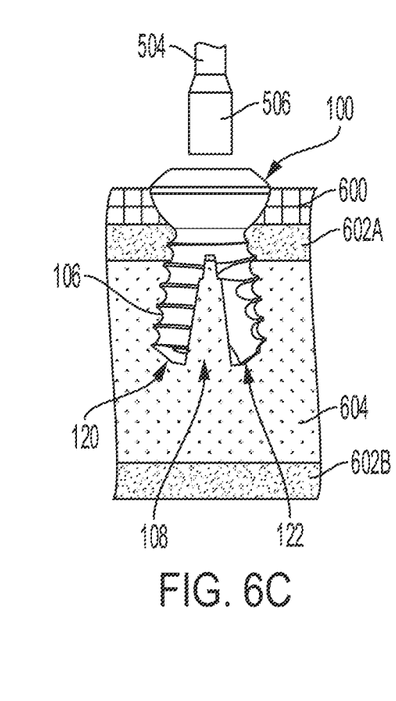

FIGS. 6A to 6C illustrate steps of an example method for installing a bone rivet (e.g., the bone rivet 100) into bone. In some instances, the bone rivet 100 may secure a plate 600 to bone as shown in FIGS. 6A to 6C, though the example method may apply similarly to other instances in which the plate 600 is not present. A surgeon may drill a bone hole 606 into bone through the first cortex 602A of the bone. In some aspects, the surgeon may drill the bone hole 606 through the first cortex 602A, the medullary canal 604, and the second cortex 602B of the bone.

In at least some instances, the surgeon may determine a desired size of the bone rivet 100 using a suitable measuring tool. The bone rivet 100 of the desired size may then be loaded with a mandrel 502 if not already loaded. As mentioned above, the bone rivet 100 is loaded with the mandrel 502 when the rod 504 is positioned through the channel 110 and the leading end of the bone rivet 100 is adjacent the bulb 506. In various aspects, the surgeon may insert the bone rivet 100 having a loaded mandrel 502 into the bone hole 606. In some examples, the bone rivet 100 having the loaded mandrel 502 is loaded into a bone rivet deployment tool, such as a bone rivet gun, and the tool is used to insert the bone rivet 100 having the loaded mandrel 502 into the bone hole 606.

In one aspect of the present disclosure, the mandrel 502 and/or the bone rivet 100 may be constructed such that they can be used to form a hole in a bone under the power of a drill without the need for pre-drilling prior to insertion. For instance, a tip of the bulb 506 of the mandrel 502 may be a trocar tip or a pointed tip with cutting flutes. In some aspects, the threaded shaft 104 of the bone rivet 100 may include an additional cutting flute at the leading edge of the threaded shaft 104 to aid in drilling.

In an example of such various aspects, the bone rivet 100 with a loaded mandrel 502 may be coupled to a powered drill that drives the bone rivet 100 and loaded mandrel 502 to form the bone hole 606. In some instances, the bone rivet 100 with the loaded mandrel 502 may be removed from the bone hole 606 after formation, de-coupled from the powered drill, and then re-inserted into the bone hole 606. In other instances, the bone rivet 100 remains in the bone hole 606 after formation (i.e. it is not removed) and only the mandrel 502 is removed to install the bone rivet 100. In some aspects, a bone rivet deployment tool may be used with the bone rivet 100 and loaded mandrel 502 to install the bone rivet 100 in bone hole 606. Because the drilling is done under high rotational speeds, the bone hole 606 formed by the bone rivet 100 and loaded mandrel 502 is smooth and therefore does not include a thread path despite the threaded shaft 104 of the bone rivet 100 being inserted in the bone hole 606 during formation. Accordingly, this aspect of the provided method still provides the advantage of aiding the removal of the installed bone rivet 100 from bone once installed as compared to at least some typical bone rivets. Additionally, this aspect of the provided method has the advantage of eliminating the need for pre-drilling, thus reducing operative time further.

With the bone rivet 100 and loaded mandrel 502 inserted in the bone hole 606, the surgeon may translate the mandrel 502 through the channel 110 and out of the bone rivet 100 in the direction of the arrow 608 to install the bone rivet 100. In at least some aspects, the surgeon translates the mandrel 502 through the channel 110 and out of the bone rivet 100 using the bone rivet deployment tool. As the surgeon translates the mandrel 502 through the channel 110, the bulb 506 initially passes through the second portion 118 of the channel 110. Since the bulb 506 has a greater width than the second portion 118, as described above, the bulb 506 forces the threaded shaft 104 of the bone rivet 100 to deform as the bulb 506 passes through the second portion 118 of the channel 110. In this example, the bulb 506 forces the wing 120 and the wing 122 to bend away from one another. The thread 106 on each of the bent wings 120 and 122 presses into the bone and provides holding power for the bone rivet 100. Once the bulb 506 reaches the first portion 116 of the channel 110 as the mandrel 502 is translated out of the bone rivet 100, the bulb 506 no longer forces the bone rivet 100 to deform, as described above. In various aspects, the entire mandrel 502 is removed from the bone rivet 100 and the patient, and can be disposed of or cleaned for later use.

Although it can be beneficial to remove the entire mandrel 502 from the patient so that there are no potentially loose pieces in the patient, it is also contemplated in one aspect of the present disclosure, that a portion of the mandrel 502 could remain between the wings 120 and 122 after installation of the bone rivet 100 to help maintain the bend in the wings 120 and 122. For instance, the mandrel 502 may include a reduced portion at which the rod 504 is configured to break upon a force being applied, such as a twisting force. In one example, this reduced portion may be where the rod 504 meets the bulb 506. In such an example, once the mandrel 502 has been translated through the channel 110 to sufficiently bend the wings 120 and 122, a surgeon may twist the rod 504 to separate it from the bulb 506 thereby leaving the bulb 506 between the wings 120 and 122.

In some aspects, the example method may include removing the installed bone rivet 100 from the bone hole 606. In such aspects, the surgeon may engage the driver interface 114 of the bone rivet 100 with a drive instrument and rotate the bone rivet 100 so that the thread 106 drives the bone rivet 100 out of the bone hole 106. As described above, the cutting flute 112 cuts into the bone as the surgeon rotates the bone rivet 100 with the drive instrument to form an interior thread in the bone, thereby reducing an amount of torque the surgeon must apply to rotate and remove the bone rivet 100.

Figure 7A:
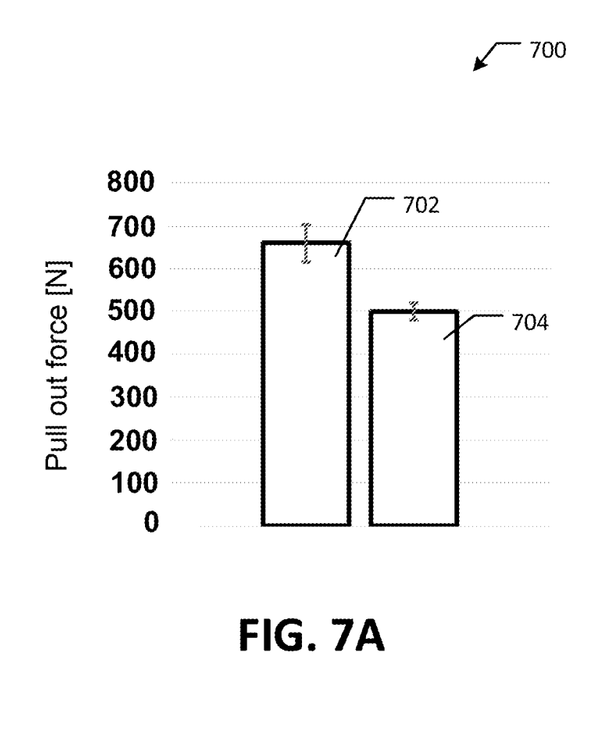
FIG. 7A illustrates a bar graph showing an average magnitude and standard deviation of the pullout force for typical bone screws as compared to the provided bone rivet.
Figure 7B:
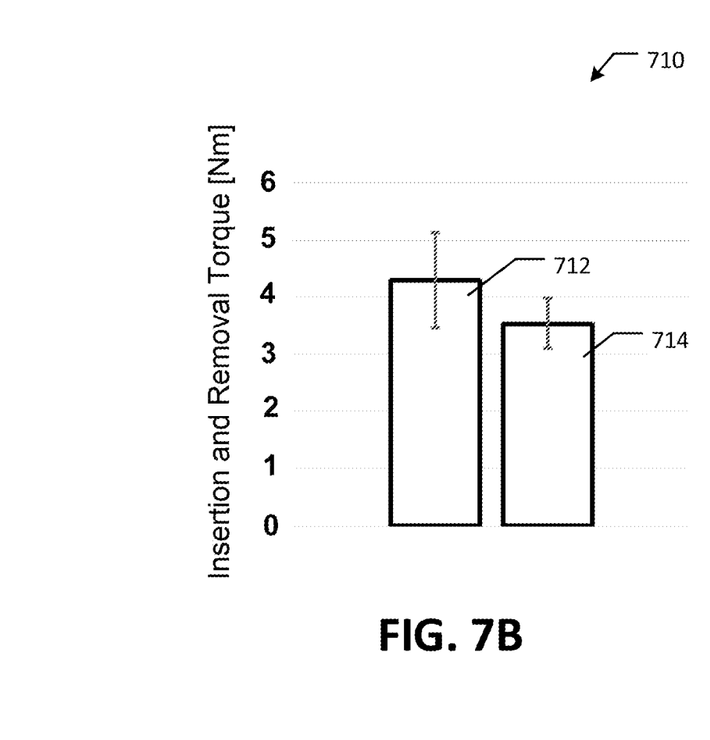
FIG. 7B illustrates a bar graph showing an average magnitude and standard deviation of the torque required to insert typical bone screws as compared to that required to remove the provided bone rivet.

The inventors have demonstrated that the bone rivet 100 of the present disclosure provides a pull out strength on the same order of magnitude as a typical, comparably-sized bone screw. FIG. 7A illustrates a bar graph 700 showing an average magnitude of the pullout force (in Newtons) for eight 8 mm bone screws (shown by the bar 702) as compared to the provided bone rivet 100 (shown by the bar 704). A standard deviation is also shown for each the bar 702 and the bar 704. The inventors have additionally demonstrated that the torque required to remove the bone rivet 100 of the present disclosure from a bone is on the same order of magnitude as the torque required to insert a typical, comparably-sized bone screw. FIG. 7B illustrates a bar graph 710 showing an average magnitude of the torque (in Newton-meters) required to insert eight 8 mm bone screws (shown by the bar 712) as compared to that required to remove the provided bone rivet 100 (shown by the bar 714). A standard deviation is also shown for each the bar 712 and the bar 714.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention claimed is:

1. A bone rivet comprising:
a body portion including a head and a threaded shaft, wherein a portion of the threaded shaft is deformable such that a width of the portion of the threaded shaft after deformation is greater than a width of the threaded shaft prior to deformation,
wherein a channel extends through the body portion, the channel including a first portion and a second portion, the first portion having a greater width than the second portion, and the first portion of the channel extending through the head of the body portion,
wherein the body portion is constructed of a material such that the portion of the threaded shaft deforms upon forced expansion and subsequently maintains that deformation, and
wherein the threaded shaft includes a cutting flute extending along a full length of the portion of the threaded shaft that is deformable.

2. The bone rivet of claim 1, wherein the threaded shaft includes a slit thereby separating the portion of the threaded shaft into a first wing and a second wing, and wherein the first wing and the second wing bend away from one another upon forced expansion of the portion of the threaded shaft.

3. The bone rivet of claim 2, wherein the first portion of the channel begins near a termination point of the slit and between the termination point of the slit and the leading end of the bone rivet.

4. The bone rivet of claim 2, wherein the cutting flute is located adjacent the slit at an edge of the first or second wing.

5. The bone rivet of claim 2, wherein the cutting flute is located away from an edge of the first wing and from an edge of the second wing.

6. The bone rivet of claim 1, wherein a length of the second portion of the channel is less than or equal to a length of the threaded shaft.

7. The bone rivet of claim 1, wherein the threaded shaft includes more than one thread.

8. The bone rivet of claim 1, wherein the threaded shaft includes more than one slit thereby separating the threaded shaft into three or more wings.

9. A bone rivet installation system comprising:
a mandrel including a rod and a bulb at a distal end of the mandrel, the bulb having a greater width than the rod; and
a bone rivet including:
a body portion including a head and a threaded shaft, wherein a portion of the threaded shaft is deformable such that a width of the portion of the threaded shaft after deformation is greater than a width of the threaded shaft prior to deformation,
wherein a channel extends through the body portion, the channel including a first portion and a second portion, the first portion having a greater width than the second portion, and the first portion of the channel extending through the head of the body portion,
wherein the body portion is constructed of a material such that the portion of the threaded shaft deforms upon forced expansion of the portion of the threaded shaft and subsequently maintains that deformation, and
wherein the threaded shaft includes a cutting flute extending along a full length of the portion of the threaded shaft that is deformable,
wherein the width of the bulb is greater than the width of the second portion of the channel and less than the width of the first portion of the channel.

10. The bone rivet installation system of claim 9, wherein the rod of the mandrel includes a reduced portion at which the rod is configured to break upon a force being applied.

11. The bone rivet installation system of claim 9, wherein the first portion of the channel begins between the head and a termination point of the portion of the threaded shaft that is deformable.

12. The bone rivet installation system of claim 9, wherein the bone rivet is configured such that a portion of the threaded shaft fractures when the portion of the threaded shaft is deformed.

* * * * *